United States Patent
Shimko

(10) Patent No.: US 9,358,323 B2
(45) Date of Patent: Jun. 7, 2016

(54) FLOWABLE CERAMIC PUTTY

(75) Inventor: Daniel A. Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 109 days.

(21) Appl. No.: 13/695,109

(22) PCT Filed: Apr. 28, 2011

(86) PCT No.: PCT/US2011/034301
§ 371 (c)(1),
(2), (4) Date: Oct. 29, 2012

(87) PCT Pub. No.: WO2011/137231
PCT Pub. Date: Nov. 3, 2011

(65) Prior Publication Data
US 2013/0045920 A1   Feb. 21, 2013

Related U.S. Application Data

(60) Provisional application No. 61/329,179, filed on Apr. 29, 2010.

(51) Int. Cl.
| | |
|---|---|
| A61K 47/36 | (2006.01) |
| A61K 38/18 | (2006.01) |
| A61K 31/74 | (2006.01) |
| A61P 19/08 | (2006.01) |
| A61L 27/26 | (2006.01) |
| A61L 24/00 | (2006.01) |
| A61L 27/46 | (2006.01) |
| A61L 27/54 | (2006.01) |

(52) U.S. Cl.
CPC ............. *A61L 27/26* (2013.01); *A61L 24/0084* (2013.01); *A61L 27/46* (2013.01); *A61L 27/54* (2013.01); *A61L 2300/414* (2013.01)

(58) Field of Classification Search
None
See application file for complete search history.

(56) References Cited

U.S. PATENT DOCUMENTS

| 5,385,887 A * | 1/1995 | Yim et al. ....................... 514/8.8 |
| 5,422,340 A * | 6/1995 | Ammann et al. .............. 424/489 |
| 2003/0180376 A1 | 9/2003 | Dalal et al. |
| 2005/0177245 A1 | 8/2005 | Leatherbury et al. |
| 2007/0225811 A1 | 9/2007 | Scifert et al. |
| 2008/0147197 A1 | 6/2008 | McKay |
| 2009/0149873 A1 * | 6/2009 | Zhou et al. ..................... 606/151 |
| 2009/0238758 A1 | 9/2009 | Wellisz et al. |
| 2010/0098762 A1 * | 4/2010 | Han et al. ....................... 424/486 |

OTHER PUBLICATIONS

ALGISORB Calcium Alginate Dressing (date unknown). Retrieved Dec. 27, 2013, from http://www.skawamoto.com/Upload/Products/200810993631288.pdf.*
Augst et al. Alginate hydrogels as biomaterials. Macromol Biosci. Aug. 7, 2006;6(8):623-33.*
Clokie CM, Urist MR. Bone morphogenetic protein excipients: comparative observations on poloxamer. Plast Reconstr Surg. Feb. 2000;105(2):628-37.*
Author Corrections, in: J Craniofac Surg. May 2008;19(3):871.*
Fowler et al. Evaluation of pluronic polyols as carriers for grafting materials: study in rat calvaria defects. J Periodontol. Feb. 2002;73(2):191-7.*
Gombotz et al. Protein release from alginate matrices. Adv Drug Deliv Rev. May 4, 1998;31(3):267-285.*
Luginbuehl et al. Insulin-like growth factor I-releasing alginate-tricalciumphosphate composites for bone regeneration. Pharm Res. Jun. 2005;22(6):940-50. Epub Jun. 8, 2005.*
Poloxamer 407. (Mar. 7, 2013). In Wikipedia, The Free Encyclopedia. Retrieved 02:07, Dec. 27, 2013, from http://en.wikipedia.org/w/index.php?title=Poloxamer_407&oldid=542551598.*
U.S. Appl. No. 13/458,286, filed Apr. 27, 2012.*
Zhou et al. An evaluation of hydroxyapatite and biphasic calcium phosphate in combination with Pluronic F127 and BMP on bone repair. J Craniofac Surg. Nov. 2007;18(6):1264-75.*
Kenley et al. Osseous regeneration in the rat calvarium using novel delivery systems for recombinant human bone morphogenetic protein 2 (rhBMP 2). J Biomed Mater Res. Oct. 1994;28(10):1139-47.*
International Search Report and Written Opinion for PCT/US2011/34301 the counterpart application mailed on Jul. 7, 2011.

* cited by examiner

*Primary Examiner* — David Romeo
(74) *Attorney, Agent, or Firm* — Sorell Lenna & Schmidt LLP

(57) ABSTRACT

The invention relates to a composition comprising an aqueous admixture of ceramic particles, polysaccharide, a therapeutic agent and, optionally, a polymer, and methods of using the same. The present invention provides a flowable bone void filler for use in medical situations where bone regeneration is desired. In an exemplary embodiment the bone void filler comprises a polysaccharide, a ceramic material and a polymer that exhibits thermosetting properties such that it exists as a viscous liquid at room temperatures and as a gel at about body temperature. In another exemplary embodiment the bone void filler comprises a polysaccharide, a ceramic material, a polymer that exhibits thermosetting properties such that it exists as a viscous liquid at room temperature and as a gel at about body temperatures, and a therapeutic agent.

16 Claims, No Drawings

FLOWABLE CERAMIC PUTTY

This application is a U.S. National Stage filing under 35 U.S.C. 371 of copending PCT Application Serial No. PCT/US2011/034301, filed Apr. 28, 2011, which claims the benefit of priority to U.S. provisional patent application no. 61/329,179, filed Apr. 29, 2010, both of which applications are incorporated herein by reference to the extent that they do not conflict with the present disclosure.

BACKGROUND

A wide variety of implant formulations have been suggested in the art for the treatment of bone defects. In addition to traditional bone grafting, a number of synthetic bone graft substitutes have been used or explored, including malleable putties. In particular, malleable putties may be used to fill bone voids and stimulate regeneration of bone in a subject. The use of a composition having putty-like consistency facilitates the placement of the bone void filler into the bone defect site, which is frequently an irregular shape. To fill these voids, surgeons may take a bone void filler and trowel it into the defect or shape it by hand.

Many products have been developed in an attempt to treat this surgical need for a biocompatible bone putty, for example, autologous bone particles recovered from the patient are wet and viscous from the associated blood and this is packed into the bone void. While autologous bone is considered to be the gold-standard for healing bone defects, it requires significant additional surgery that results in potential adverse events associate with such surgery, which in extreme cases includes death.

Implant materials can benefit from the presence of scaffolding material, such as, biocompatible ceramics or other mineral scaffolds. However, biocompatible ceramics are generally hard, brittle substances, which makes it difficult to incorporate substantial levels into a composition that has a putty-like consistency. Addition of hard pieces of ceramic tend to disrupt the putty mass, producing a composition that is crumbly and lacks the cohesiveness desired for handling prior to implantation and for persistence after implantation.

Proteins, such as BMP-2, GDF-5 and BMP-7, have been shown to induce bone growth, but such bone growth is desirably restricted to a particular location in the subject being treated. Hence, it is preferable to confine these proteins to the desired treatment site. Unfortunately, this has proven difficult to do and as a result the use of these proteins has either been limited or has required a large amount of the protein to achieve the desired result.

What is needed is a moldable or flowable implant composition that may be used to apply therapeutic agents to a local area and retain them there for a prolonged period of time, for example, at least a week.

Any publications or references discussed herein are presented to describe the background of the invention and to provide additional detail regarding its practice.

Nothing herein is to be construed as an admission that the inventors are not entitled to antedate such disclosure by virtue of prior invention. Should there be a conflict, or apparent conflict, between the specification and any of the incorporated references, the specification takes precedence and the conflicting or apparently conflicting aspect of the reference is to be disregarded.

SUMMARY OF THE INVENTION

In an exemplary embodiment, the present invention provides a flowable bone void filler for use in medical situations where bone regeneration is desired. In an exemplary embodiment the bone void filler comprises a polysaccharide, a ceramic material and a polymer that exhibits thermosetting properties such that it exists as a viscous liquid at room temperatures and as a gel at about body temperature. In another exemplary embodiment the bone void filler comprises a polysaccharide, a ceramic material, a polymer that exhibits thermosetting properties such that it exists as a viscous liquid at room temperature and as a gel at about body temperatures, and a therapeutic agent. In another exemplary embodiment the bone void filler comprises a polysaccharide, a ceramic material and a polyethyleneoxide (PEO)/polypropyleneoxide (PPO)/polyethyleneoxide (PEO) (PEO/PPO/PEO type polymer). In another exemplary embodiment the bone void filler comprises a polysaccharide, a ceramic material, a polyethyleneoxide (PEO)/polypropyleneoxide (PPO)/polyethyleneoxide (PEO) (PEO/PPO/PEO type polymer) and a therapeutic agent. In another exemplary embodiment the bone void filler comprises alginate, ceramic particles and a PEO/PPO/PEO block polymer. In yet another exemplary embodiment the bone void filler comprises alginate, ceramic particles, a PEO/PPO/PEO block polymer and a therapeutic agent. An example of a suitable PEO/PPO/PEO block polymer is Pluronic F-127 (Poloxamer 407, PF-127). In one aspect of the invention, the ceramic particles are bound together by the gel-like consistency of the thermosetting polymer and polysaccharide, without chemical cross-linking. Optionally, the bone void filler may comprise at least one dry or powder component and at least one liquid component in proportions such that the combination of the at least one dry component and the at least one liquid component produce a bone void filer having a putty like consistency.

In another exemplary embodiment, the bone void filler comprises a polysaccharide, a ceramic material and a therapeutic agent. In another exemplary embodiment the product comprises alginate, a ceramic material and a therapeutic agent. In another exemplary embodiment, the bone void filler comprises alginate, tricalcium phosphate and a therapeutic agent comprising at least one Bone morphogenic protein and/or Growth Differentiation factor.

In another exemplary embodiment, the ceramic of the invention is α-tricalcium phosphate (TCP), β-TCP, and/or hydroxyl apatite (HA), which may or may not include substitutions, such as silicon substituted calcium phosphate or TCP. In another exemplary embodiment, the composition of the invention does not contain a readily dissolvable source of calcium within the composition, for example TCP and HA are slow dissolving sources of calcium, whereas calcium sulfate is a readily dissolvable source of calcium.

Therapeutic agents that may be used in the invention include, but are not limited to, members of the TGF-β family of proteins, such as TGF-β1, TGF-β2, TGF-β3, TGF-β4, TGF-β5 (see e.g.: U.S. Pat. No. 5,284,763; EP 0376785; and U.S. Pat. No. 4,886,747), GDF-12 (see WO 96/02559), BMP-2 (BMP-2a), BMP-3, BMP-3b, BMP-4 (BMP-2b), BMP-5, BMP-6, BMP-7 (OP-1), BMP-8 (OP-2), BMP-9, BMP-10, BMP-11, BMP-12, BMP-13 (see WO 93/00432; WO 94/26893; WO 94/26892, WO 95/16035), GDF-1, GDF-3, GDF-5, GDF-6, GDF-7, GDF-9, GDF-10, GDF-11, VEGF-A, VEGF-B, VEGF-C, VEGF-D, VEGF-E, CTGF-1, CTGF-2, CTGF-3, anti-TNFα, PDGF-A, PDGF-B, PDGF-C, PDGF-D, LIM mineralization protein, IGF-I, IGF-II, FGF, beta-2-microglobulin, and/or combinations thereof. The therapeutic agents may be recombinant human proteins, since they may be produced in a relatively unlimited supply, are non-immunogenic and do not transmit infectious diseases. In an exemplary embodiment, the bone morphogenetic protein is a rhBMP-2, rhBMP-4, rhBMP-7, GDF-5, heterodimers and/or homodimers thereof. In an exemplary embodiment, the therapeutic agent comprises a recombinant human BMP-2, GDF-5 and/or BMP-7. See also U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. (see: U.S. Pat. Nos. 7,365,051; 5,013,649; International patent publications WO 88/00205; WO 89/10409; WO 90/11366; WO 91/05802; WO 92/15323; WO 91/18098; WO 93/00432; WO 93/09229; WO 94/01557; WO 94/26893; WO 94/26892; WO 94/15949; WO 95/01801; WO 95/01802 and EP 0 626 451).

Polysaccharides of the invention include, but are not limited to, alginates, chitosans, starch, glycogen, cellulose, chitin, arabinoxylans, Acidic polysaccharides, bacterial polysaccharides, bacterial capsular polysaccharides and combinations thereof.

In another exemplary embodiment, the invention provides a method to promote bone repair and regeneration. The method comprises preparing a composition described herein, applying the composition to a bone defect, and allowing regeneration of bone in the defect area.

In yet another exemplary embodiment, the invention provides a medical kit comprising a first container and a second container wherein the first container comprises a mixture of a polysaccharide and ceramic, optionally a polymer that exhibits thermosetting properties may also be present, and the second containers comprises an aqueous diluent which may or may not have the therapeutic agent dissolved in it. In an exemplary embodiment, the kit contains a first container comprising a polysaccharide and a ceramic (optionally it may also include a thermosetting polymer), a second container comprising a diluent and a third container comprising a lyophilized protein, such as BMP-2, OP-1, and/or GDF-5, wherein the components in the kit are present in an amount such that when the lyophilized protein is reconstituted in the diluent and the diluent/protein mixture is added to the polysaccharide and ceramic (which may include an additional thermosetting polymer) the resulting mixture has a putty like consistency. Optionally, the kit may include an additional container comprising an aqueous solution of a divalent cation, for example, a calcium chloride solution (see, US Patent Pub. 2007254042 and US Patent Pub. 20110028393, which is co-owned U.S. application Ser. No. 12/512,651, filed Jul. 30, 2009. Optionally the therapeutic agent may be admixed with the polysaccharide and ceramic in a first container and rehydrated using an aqueous diluent present in a second container, wherein the mixture produces a bone void filler having a putty like consistency. For example, alginate, ceramic, a lyophilized thereapeutic agent, such as BMP-2 or GDF-5, and poloxamer 407 may be present in a first container or area in a container, an aqueous solution may be present in a second container or area in a container, wherein the first and second containers or areas are adapted to connect such that the aqueous solution and powder may mix and the wetted mixture may be introduced into a subject (see U.S. Pat. Nos. 6,267,154, and 5,328,462). In another exemplary embodiment, the kit contains a first container comprising a polysaccharide, a ceramic and a diluent (optionally it may also include a thermosetting polymer), a second container comprising a therapeutic agent, for example, a lyophilized protein such as BMP-2, OP-1, and/or GDF-5, wherein the therapeutic agent may be mixed with the carrier prior to application to a subject. In an exemplary embodiment, the aqueous solution or diluent may be phosphate buffered saline, physiological saline, water, a buffer, blood, bone marrow aspirate or a combination thereof.

The components of the kits described herein may be delivered in vials, syringes, or other suitable containers know in the art. Some or all of the components may be aseptically produced or terminally sterilized to minimize or eliminate the bioburden. Storage may be at room temp, refrigerated, frozen, or ultra-cold to retain functionality of the materials.

In another exemplary embodiment, the invention provides a dry admixture including a polysaccharide and a ceramic, wherein the polysaccharide to ceramic ratio is between about 1:1 and about 1:20, about 1:1 to about 1:10, about 1:2 to about 1:10, about 1:3 to about 1:8, expressed as dry weight. The composition may also include a thermosetting polymer in a weight ratio of polysaccharide to thermosetting polymer of about 1:1 to about 1:20, about 1:2 to about 1:10, about 1:3 to about 1:10, about 1:6 to about 1:8. The composition may also include a therapeutic agent in a weight ratio of polysaccharide to therapeutic agent of about 1:0.001 to about 1:0.1, about 1:0.003 to about 1:0.04, about 1:0.01 to about 1:0.04, about 1:0.0000001 to about 1:0.6, about 1:0.00001 to about 1:0.3, about 1:0.0001 to about 1:0.16, or about 1:0.001 to about 1:0.08.

In another exemplary embodiment, the composition may be formed into a shape, e.g., placed in a bone void or molded into a shape, and the exterior surface may be treated with a divalent cation, such as a divalent calcium cation, zinc, copper, strontium, iron(II) and/or magnesium. Such a surface treatment produces a relatively thin film of cross-linked alginate on the surface of the implant that may serve to anchor the graft to surrounding tissues, prevent cellular infiltration into the graft, and/or slow dissolution or reabsorption of the composition and/or components of the composition.

In still a further exemplary embodiment, the invention provides methods of treating patients comprising implanting in a patient a composition as described herein, and kits including such compositions packaged in sterile condition.

In yet another exemplary embodiment, the implant compositions may be mixed with autograft, blood, blood derivatives, such as platelets and/or stem cells, bone marrow, bone marrow extract and bone marrow derivatives, such as platelets and/or stem cells. In another exemplary embodiment, the ceramic material may include a tricalcium phosphate ($\alpha$ and/or $\beta$), hydroxyapatite, Bioglass®, biphasic calcium phosphate, corraline hydroxyapatite, and other biocompatible ceramics. Biphasic calcium phosphate is a particular synthetic ceramic that may be used in the invention, for example, a tricalcium phosphate:hydroxyapatite mixture with a weight ratio of about 50:50 to about 95:5, about 70:30 to about 95:5, about 80:20 to about 90:10, or about 85:15. The calcium phosphate material may be in a granular form having an average particle diameter between about 0.001 and 4.0 mm, between about 0.002 and 2.0 mm, between about 0.01 and 1.0 mm or between about 0.02 and 0.5 mm.

In yet another exemplary embodiment, one or more porogens may be added. Porogens may be made of any biocompatible, biodegradable substance that can be formed into a particle and that is capable of at least substantially retaining its shape during the manufacturing of the implant, but that is subject to rapid degradation or dissolution when placed in contact with an aqueous solution, such as an in vivo environment. The porogens may be inorganic or organic, for example, they may be made from gelatin, an organic polymer (e.g., polyvinyl alcohol), polyurethanes, polyorthoesters, PLA, PGA, and PLGA copolymers, a saccharide, a calcium salt, sodium chloride, calcium phosphate or mixtures thereof.

Porogen particles may be about 100 to about 500 microns. In one embodiment, all porogen particles of a given morphology can have at least one average axial, transverse, or lateral dimension that is about 100 to about 500 microns. In some embodiments, all porogen particles used can independently have at least one axial, transverse, or lateral dimension that is about 100 to about 500 microns. In some embodiments, all porogen particles used can collectively have at least one average axial, transverse, or lateral dimension that is about 100 to about 500 microns.

In some embodiments, at least one dimension of the porogen particles can be about 100 microns or more, or about 120 microns or more, or about 140 microns or more. In some embodiments, at least one dimension of the porogen particles can be about 500 microns or less, about 425 microns or less, about 350 microns or less, about 300 microns or less, or about 250 microns or less. In some embodiments, the porogen particles can have at least one dimension that is about 120 to about 400 microns.

Additional exemplary embodiments, as well as features and advantages thereof, will be apparent to those skilled in the art from the descriptions herein.

DETAILED DESCRIPTION OF THE INVENTION

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated bone void filler, and such further applications of the principles of the invention as described herein being contemplated as would normally occur to one skilled in the art to which the invention relates.

The uses of the terms "a" and "an" and "the" and similar references in the context of describing the invention (especially in the context of the following claims) are to be construed to cover both the singular and the plural, unless otherwise indicated herein or clearly contradicted by context.

As used herein, "biocompatible" means the material used elicits little or no immune response in vivo and has no significant undesirable or injurious effects on a biological system or organism.

As used herein, a "thermosetting polymer" means a polymer having a phase transition temperature above about room temperature (about 22-25° C.) that transitions to a gel like state at about body temperature (about 37° C.).

As used herein, a "bone void filler," or similar phrases, means a flowable or moldable composition that can be flowed or molded into a bone defect, such as a crack, fissure, gap or the like, such as a gap between a synthetic implant (such as a metal prosthesis) and a bone and where bone regeneration is desirable.

Recitation of ranges of values herein are merely intended to serve as a shorthand method of referring individually to each separate value falling within the range, unless otherwise indicated herein, and each separate value is incorporated into the specification as if it were individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of and "consisting essentially of."

As used herein, "about" means approximately or fairly close to.

The term "ceramic" refers to a biologically compatible calcium phosphate based composition such as tricalcium phosphate ($\alpha$ and/or $\beta$), hydroxyapatite, silicon substituted tricalcium phosphate, silicon substituted hydroxyapatite, calcium pyrophosphate, combinations thereof and similar compositions.

As used herein, "mammal" means a warm-blooded vertebrate animal of the class Mammalia, including, but not limited to, humans, primates (such as chimpanzees, apes, orangutans and monkeys), rats, mice, rabbits, sheep, cats, dogs, cows, horses, etc.

As used herein, a "therapeutically effective amount" or "effective amount" means an amount that when administered results in alteration of the biological activity, such as, for example, promotion of bone, cartilage and/or other tissue (e.g., vascular tissue) growth, inhibits inflammation, reduces or alleviates pain, or has a desired effect in the subject. A therapeutically effective amount will vary depending upon a variety of factors, including the agents pharmacokinetic properties, the route of administration, patient conditions and characteristics (sex, age, body weight, health, size, etc.), extent of symptoms, concurrent treatments, frequency of treatment and the effect desired.

The weight of compounds used herein is provide in the absence of water, hence a composition comprising about 41% dry weight Pluronic F127, 7% dry weight Ultra Pure MVG Sodium Alginate, 53% dry weight Beta-tricalcium phosphate, and a therapeutic agent would also contain a sufficient amount of an aqueous solution, such as water, to allow the compounds to be homogeneously mixed. However, the weight percents are expressed as the dry weight without regard to the amount of water used to dissolve the compounds and produce a flowable substance, since the amount of water or other aqueous solution may be varied depending on the hydration state of the dry components and the desired consistency of the final product.

As described herein, in certain aspects, the present invention relates to implantable medical bone void fillers, and to methods for making and using the bone void fillers. In particular embodiments, the osteoinductive medical implants include a flowable composition incorporating a ceramic material, at least one binding agent, such as a polysaccharide and/or a thermosetting polymer, and a therapeutic agent, such as BMP-2, GDF-5, or BMP-7.

In certain embodiments, the ceramic material may have an average particle size less than about 4 mm, less than about 3 mm, less than about 2 mm, less than about 1 mm, less than about 0.5 mm, or less than about 50 µm and/or macropores less than about 1,000 µm, less than about 500 µm, less than about 300 µm, less than about 200 µm, or less than about 100 µm in diameter (assuming a generally circular cross-sectional area). For instance, the ceramic material may have particle sizes in the range of 50 to 850 µm.

Suitable thermosetting polymers include, but are not limited to, Poloxamer 407 (Pluronic F-127), Poloxamer 338 (Pluronic F-108), Poloxamer 237 (Pluronic F-87), Poloxamer 188 (Pluronic F-68), Poloxamer 124 (Pluronic L-44), Poloxamer 331 (tested up to 0.5 g/kg day-1), Reverse Poloxamers (PPO-PEO-PPO), Tetronics (PEO-PPO-EDA-PPO-PEO), Reverse Tetronics (PPO-PEO-EDA-PEO-PPO) (see U.S. Pat. No. 3,925,241). In an exemplary embodiment, the thermosetting polymer is present in a final concentration of greater than about 20% wt/vol, greater than about 22% wt/vol, greater than about 25% wt/vol, or greater than about 30% wt/vol.

Suitable polysaccharides include, but are not limited to, plant-derived polysaccharides such as alginates, chitosan, pectins, starch, glycogen, cellulose, chitin, arabinoxylans, Acidic polysaccharides, bacterial polysaccharides, bacterial capsular polysaccharides and derivatives thereof. Aqueous solutions of such polysaccharides can form ionically cross-linked gels upon contact with aqueous solutions of counter-ions. For instance, useful agents for ionically cross-linking alginate and pectin polysaccharides include cationic gelling agents, preferably including divalent or trivalent cations. Useful divalent cations for these purposes include the alkaline earth metals, especially calcium and strontium, for example, calcium chloride. These ionic cross-linking agents will usually be provided as salts. Useful anionic counter-ions for the calcium or other salts are desirably selected from pharmaceutically-acceptable anions such as chlorides, gluconates, fluorides, citrates, phosphates, tartrates, sulphates, acetates, borates, and the like. An especially preferred ionic cross-linking agent for use with an alginate or pectin compound is provided by calcium chloride. The ionic polysaccharide chitosan may also be used, and may be ionically cross-linked with multivalent, anionic gelling agents. Such agents include metal polyphosphates, such as an alkali metal or ammonium polyphosphate, pyrophosphates or metaphosphates. Citrates may also be used. These anionic cross-linking agents will also usually be provided by salts. The cationic counter-ion for the polyphosphate or other salt can be any suitable, biocompatible or pharmaceutically-acceptable cation including for instance sodium, potassium, or ammonium. Many other biocompatible polysaccharides, including plant-derived and animal-derived materials, as well as corresponding ionic cross-linking agents, are known and can also be used in aspects of the present invention.

In an exemplary embodiment, the composition may be formed into a shape, e.g., placed in a bone void or molded or extruded into a shape, and the exterior surface may be treated with a divalent cation, such as a divalent calcium cation, iron(II) and/or magnesium. For example, the surface may be treated with an aqueous solution of calcium chloride. Such a surface treatment produces a relatively thin film of cross-linked alginate on the surface of the implant that may serve to slow dissolution or reabsorption of the composition and/or components of the composition, without producing sufficient cross-linking to adversely slow dissolution or reabsorption.

Additional additives include, but are not limited to, salts, sugars, analgesics, anti-inflammatory substances, antibiotics, preservatives, radiographic markera and/or other pharmaceutically acceptable excipients.

In an exemplary embodiment, the composition may be seeded with harvested bone cells, blood cells, cartilage cells, cartilage tissue and/or bone tissue, such as for example, cortical bone, autogenous bone, allogenic bones and/or xenogenic bone. For example, before insertion into the target tissue site, the composition may be wetted with bone tissue/cells, for example, bone marrow aspirated from the patient, at a ratio of about 3:1, 2:1, 1:1, 1:3 or 1:2 by volume. The bone tissue/cells are permitted to soak into the scaffolding provided, and the scaffolding may be kneaded by hand, thereby obtaining a pliable consistency that may subsequently be packed into the osteochondral defect.

External wetting agents may be applied to the devices for use in a subject, such as a mammal, for example, aqueous substances such as sterile water, physiological saline, a buffer solution (e.g., a sodium phosphate buffered solution), blood, bone marrow, bone marrow fractions or other liquid mediums, emulsions or suspensions that provide adequate wetting characteristics. Biocompatible organic liquids may also be used, alone or in combination with water.

Implant devices of the invention may also contain other beneficial substances including for example preservatives, cosolvents, suspending agents, buffering agents, viscosity enhancing agents, ionic strength and osmolality adjusters and/or other excipients.

The implant devices disclosed herein may also include other biocompatible and preferably bioresorbable substances. These materials may include, for example, natural polymers such as proteins and polypeptides, glycosaminoglycans, proteoglycans, elastin, hyaluronic acid, dermatan sulfate, Alginate, or mixtures or composites thereof.

Therapeutic agents may be delivered with devices of the invention. These therapeutic agents may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, prostaglandins, statins, antiseptics, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenlcs, non-steroidal anti-inflammatory agents, steroidal anti-inflammatory agents, antioxidants, vaso-active agents, bone-active agents, osteogenic factors, antiarthritics, and diagnostic agents.

Therapeutic agents may also include autologous or allogenic tissue, materials, such as, blood or blood fractions, bone marrow or bone marrow fractions, and/or other sources of cells or other beneficial tissue components derived from the patient to be treated or another suitable animal source. These substances may, for example, be added to the device just prior to implantation into the patient.

Therapeutic agents such as those described herein may be incorporated homogeneously or regionally into the implant devices by simple admixture, soaking or otherwise.

Desirably, the therapeutic agent will include a growth factor from a class of proteins known generally as bone morphogenic proteins (BMPs), and may in certain embodiments be recombinant human (rh) BMPs. These BMP proteins, which are known to have osteogenic, chondrogenic and other growth and differentiation activities, include rhBMP-2, rhBMP-3, rhBMP4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, BMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-l5, disclosed U.S. Pat. No. 5,635,372 and BMP-16, disclosed in U.S. Pat.

Nos. 5,965,403 and 6,331,612. Other compositions which may also be useful include Vgr-2, and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these Patents and applications are hereby incorporated herein by reference. Also useful in the present invention are heterodimers or homodimers of the above and modified proteins or partial deletion products thereof. These proteins may be used individually or in mixtures of two or more.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-beta superfamily, such as activins, inhibins and TGF-beta 1 (e.g., a heterodimer composed of one monomer each of a BMP and a related member of the TGF-beta superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon several factors including the size and nature of the defect being treated, and the device and particular protein being employed.

Other therapeutic growth factors or substances may also be used in devices of the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-α and TGF-β.

The osteogenic proteins or other therapeutic agents, when used in the present invention, may be provided in liquid formulations, for example buffered aqueous formulations. In certain embodiments, such liquid formulations may be received upon and/or within, or otherwise combined with a dry-form device by a health care provider just prior to implantation. In other embodiments, such liquid formulations may be included within wet materials used to prepare a dry-form or wetted device during its manufacture. One suitable rhBMP-2 formulation is available from Medtronic Sofamor Danek, Memphis, Tenn., with its INFUSE® Bone Graft product.

The osteogenic proteins or other therapuetic agents, when used in the present invention, may be provided as a lyophilized powder. In certain embodiments, such lyophilized powders may be combined with other dry components during manufacture. One suitable rhBMP-2 formulation is available from Medtronic Sofamor Danek, Memphis, Tenn., with its INFUSE® Bone Graft product, wherein the lyophilized protein may be combined with a polysaccharide, a ceramic and optionally a thermosetting polymer.

Osteoinductive devices of the present invention may also comprise progenitor and/or stem cells derived from embryonic or adult tissue sources and/or taken from culture or obtained from the subject. Illustratively, compositions of the invention may incorporate cells derived from blood, bone marrow, or other tissue sources from the patient to be treated (autologous cells) or from a suitable allogenic or xenogenic donor source. In certain embodiments of the invention, the device incorporates an enriched bone marrow fraction, prepared for example as described in US Patent Publication No. 2005/0130301 to McKay et al. published Jun. 16, 2005, which is hereby incorporated herein by reference in its entirety. Thus, implantable materials may incorporate a bone marrow fraction enriched in connective tissue growth components, that is prepared by centrifuging a biological sample (e.g. from the patient to be treated) to separate the sample into fractions including a fraction rich in connective tissue growth components. The fraction rich in connective tissue growth components may then be isolated from the separated sample, and incorporated into or onto a dry-form device of the invention, e.g. by using the fraction in or as a wetting medium applied to the device by a health care provider prior to implantation.

Osteoinductive devices of the present invention may also comprise suitable biostatic/biocidal agents including, but not limited to, antibiotics, such as, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, moxifloxacin, metronidazole benzoate, spectinomycin, tobramyc in, paromomycin, metronidazole, tinidazole, ornidazole, amifloxacin, cinoxacin, ciprofloxacin, difloxacin, enoxacin, fleroxacin, norfloxacin, ofloxacin, temafloxacin, teromyocin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, povidone, sugars, mucopolysaccharides, chlorobutanol, quarternary ammonium compounds such as benzalkonium chloride, organic mercurials, parahydroxy benzoates, aromatic alcohols, halogenated phenols, sorbic acid, benzoic acid, dioxin, EDTA, BHT, BHA, TBHQ, gallate esters, NDGA, tocopherols, gum guaiac, lecithin, boric acid, citric acid, p-Hydroxy benzoic acid esters, propionates, Sulfur dioxide and sulfites, nitrates and nitrites of Potassium and Sodium, diethyl pyrocarbonate, Sodium diacetate, diphenyl, hexamethylene tetramine o-phenyl phenol, and Sodium o-phenylphenoxide, etc. When employed, biostatic/biocidal agent will typically represent from about 1 to about 25 weight percent of the bone particle containing composition, calculated prior to forming the shaped material. For example, the device may include one or more antibiotic drugs.

Osteoinductive devices of the present invention may also comprise suitable surface active agents, such as biocompatible nonionic, cationic, anionic and amphoteric surfactants and mixtures thereof. When employed, surface active agent will typically represent from about 1 to about 20 weight percent of the bone particle containing composition, calculated prior to forming the shaped material.

In still further embodiments, the present invention provides methods for treating a subject that involve implanting in the subject an osteoinductive composition as described herein. In such uses, an osteoinductive composition may be implanted at a site at which bone growth is desired, e.g. to treat a bone disease, defect or location of trauma, and/or in some instances to promote artificial arthrodesis. The compositions of the invention may be used as surgical implants at, in, on, or near bone defect sites, cartilage repair sites, or other musculoskeletal sites. In certain beneficial embodiments, the composition will exhibit a conformable or flexible character that enables its introduction and shaping within voids, defects or other areas in which new tissue growth is desired, and/or in certain embodiments in which the delivery of a bioactive agent is desired.

Illustrative bone repair sites that may be treated with compositions of the invention include, for instance, those resulting from injury, defects brought about during the course of surgery, infection, malignancy or developmental malformation. The devices may be used in a wide variety of orthopedic, periodontal, neurosurgical and oral and maxillofacial surgical procedures including, but not limited to: the repair of a simple fracture, compound fracture or non-union; as an external fixation device or internal fixation device; for joint reconstruction, arthrodesis, arthroplasty or cup arthroplasty of the hip; for femoral or humeral head replacement; for femoral head surface replacement or total joint replacement; for repair of the vertebral column, spinal fusion or internal vertebral fixation; for tumor surgery; for deficit filling; for discectomy; for laminectomy; for excision of spinal cord tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; and, for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones and/or metatarsal bones.

In accordance with certain aspects of the invention, the osteoinductive composition may be used as a bone void filler, or may be incorporated in, on or around load bearing or space preserving implants such as dental implants, reconstructive meshes, orthopedic plates, maxillofacial plates, spinal implants, hip implants (e.g. in or around implant stems and/or behind acetabular cups), knee implants (e.g. in or around stems). The compositions may be incorporated in, on or around a load-bearing spinal implant device having a compressive strength of at least about 10000 N, such as a fusion cage, dowel, or other device potentially having a pocket, chamber or other cavity for containing the osteoinductive composition, and used in a spinal fusion such as an interbody fusion. One illustration of such use is in conjunction with a load-bearing interbody spinal spacer to achieve interbody fusion. In these applications, the composition may be placed in and/or around the spacer to facilitate the fusion.

The present invention also provides medical kits and/or other products that include one or more osteoinductive compositions of the invention. Such products may include the composition(s) of the invention, received in sterile condition in medical packaging. Such products may also include one or more additional surgical instruments or implants, for example a load-bearing implant (e.g. a spinal spacer), and/or a fluid transfer device such as a syringe, and/or a therapeutic substance.

In an exemplary embodiment, the present invention provides a method of forming an osteogenic osteoimplant, the method comprising: providing a mass of ceramic particles in combination with a thermosetting polymer.

EXAMPLE 1

| Reagents | Weight % |
| --- | --- |
| Pluronic F127 | 41% |
| Ultra Pure MVG Sodium Alginate | 7% |
| β-tricalcium phosphate | 53% |

In a second container the therapeutic agent is added to an aqueous solution. Where the therapeutic agent comprises recombinant human GDF-5 at a concentration of:

| rhGDF-5 | 0 mg/ml; |
| --- | --- |
|  | 0.35 mg/ml; |
|  | 0.7 mg/ml; |
|  | 1.5 mg/ml; |
| rhBMP-2 | 0 mg/ml; |
|  | 0.1 mg/ml; |
|  | 0.36 mg/ml; or |
|  | 0.71 mg/ml. |

The final product comprises 0.4 grams of dry material in combination with 0.4 mls of therapeutic agent and aqueous solution, which yields 0.7 cubic centimeters (cc) of the final product as a flowable putty. The final product comprises 23% wt/vol Pluronic F127, 4% wt/vol Alginate, 30% wt/vol β-tricalcium phosphate and a therapeutic agent.

EXAMPLE 2

| Reagents | Dry Weight % |
| --- | --- |
| Ultra Pure MVG Sodium Alginate | 25% |
| β-tricalcium phosphate | 75% |

Which is raised in 23 ml of deionized water.

In a second container the therapeutic agent is added to an aqueous solution. Where the therapeutic agent comprises recombinant human GDF-5 at a concentration of:

| rhGDF-5 | 0 mg/ml (control); |
| --- | --- |
|  | 0.35 mg/ml; |
|  | 0.7 mg/ml; or |
|  | 1.5 mg/ml; |

The final product comprises 0.75 ml of the alginate/TCP mixture in combination with 0.25 mls of therapeutic agent to yield 1 ml of the final product as a flowable putty. The final product comprises 14% wt/vol Alginate, 43% wt/vol β-tricalcium phosphate and a therapeutic agent.

EXAMPLE 3

| Reagents | Dry Weight % |
|---|---|
| Ultra Pure MVG Sodium Alginate | 25% |
| β-tricalcium phosphate | 75% |

Which is raised in 23 ml of deionized water.

In a second container the therapeutic agent is added to an aqueous solution. Where the therapeutic agent comprises recombinant human GDF-5 at a concentration of:

| rhGDF-5 | 0 mg/ml (control); |
|---|---|
| | 0.35 mg/ml; |
| | 0.7 mg/ml; or |
| | 1.5 mg/ml; |

The final product comprises 0.75 ml of the alginate/TCP mixture in combination with 0.25 mls of therapeutic agent to yield 1 ml of the final product as a flowable putty. For these implants, the flowable putty was exposed to a 1% wt/vol calcium chloride solution to produce a thin film of cross-linked alginate around the surface of the implant. The final product comprises 14% wt/vol Alginate, 43% wt/vol β-tricalcium phosphate and a therapeutic agent in an implant having a relatively thin film of cross-linked alginate surrounding it.

EXAMPLE 4

Formulation Testing

Formulations are tested using male rats. Samples are randomized so that no animal receives the same lot in both implant sites. The animals are anesthetized and prepared for surgery with pockets created in or between the muscle(s) of the hind limbs. The pockets are then filled with about 0.2 cc of the test article/sample and then the muscle pocket and skin are sutured closed. The animals are maintained in-life for 28 days.

At the end of the study duration, the animals are sacrificed and the implant site removed. Each implant is fixed, processed, and evaluated for histopathological evidence of new bone formation. Sections are taken from at least three levels of the test article within a block. The sections are mounted on slides for histological evaluation and a report is generated with scores for individual implant sites as either positive or negative relative to bone formation.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are hereby incorporated by reference in their entirety.

What is claimed is:

1. A bone void filling composition, comprising: an aqueous admixture of ceramic particles; a polysaccharide comprising alginate; a therapeutic agent; a thermosetting polymer comprising a reverse Poloxamer; and a porogen, wherein the polysaccharide and ceramic particles are present in ratio of between about 1:1 to about 1:20 by dry weight, and the porogen is organic and has a particle size of from about 120 to about 400 microns, and a film of cross-linked alginate surrounding the bone void filling composition, and the bone void filling composition comprises a viscosity enhancing agent.

2. The bone void filling composition device of claim 1, wherein the polysaccharide and ceramic particles are present in ratio of between about 1:2 to about 1:10 by dry weight.

3. The bone void filling composition of claim 1, wherein the polysaccharide and ceramic particles are present in ratio of between about 1:3 to about 1:8 by dry weight.

4. The bone void filling composition of claim 1, wherein the polysaccharide and ceramic particles are present in ratio of between about 1:2 to about 1:10 by dry weight.

5. The bone void filling composition of claim 1, wherein the polysaccharide and thermosetting polymer are present in ratio of between about 1:1 to about 1:20 by dry weight or between about 1:2 to about 1:10 by dry weight or between about 1:6 to about 1:8 by dry weight.

6. The bone void filling composition of claim 1, wherein the therapeutic agent comprises BMP-2, GDF-5 or a combination thereof.

7. The bone void filling composition of claim 6, wherein the ceramic particles are tricalcium phosphate.

8. The bone void filling composition of claim 1, wherein the thermosetting polymer is present in a final concentration of greater than about 20% wt/vol.

9. The bone void filling composition of claim 1, wherein the ceramic comprises hydroxyapatite and tricalcium phosphate or hydroxyapatite and β-tricalcium phosphate.

10. The bone void filling composition of claim 1, wherein the polysaccharide and therapeutic agent are present in a ratio of between about 1:0.0001 and about 1:0.1 by weight.

11. The bone void filling composition of claim 1, wherein the thermosetting polymer is present in a final concentration greater than about 30% wt/vol.

12. The bone void filling composition of claim 1, wherein the surface of the bone void filling composition is treated with calcium chloride such that the film of cross-linked alginate forms.

13. The bone void filling composition of claim 12, wherein the surface of the bone void filling composition is treated with 1% wt/vol of calcium chloride.

14. The bone void filling composition of claim 1, wherein the bone void filling composition comprises 14% wt/vol of alginate.

15. The bone void filling composition of claim 1, wherein the bone void filling composition further comprises bone marrow aspirate comprising bone tissue and bone cells in a 3:1 ratio by volume.

16. The bone void filling composition of claim 1, wherein the reverse Poloxamer comprises a polypropyleneoxide/polyethyleneoxide/polypropyleneoxide (PPO-PEO-PPO) block polymer.

* * * * *